United States Patent [19]

Clitherow et al.

[11] 4,317,819

[45] Mar. 2, 1982

[54] AMINE DERIVATIVES

[75] Inventors: John W. Clitherow; Barry J. Price, both of Hertford; John Bradshaw; Michael Martin-Smith, both of Ware, all of England

[73] Assignee: Glaxo Group Limited, London, England

[21] Appl. No.: 213,680

[22] Filed: Dec. 5, 1980

Related U.S. Application Data

[62] Division of Ser. No. 95,065, Nov. 16, 1979, Pat. No. 4,264,614.

[30] Foreign Application Priority Data

Nov. 16, 1978 [GB] United Kingdom ............... 44777/78

[51] Int. Cl.³ .................. A61K 31/155; A61K 31/17; C07C 127/17; C07C 129/12
[52] U.S. Cl. .................................. 424/244; 546/191; 546/213; 260/239 B; 546/214; 546/230; 260/239 BF; 546/231; 549/65; 260/244.4; 549/74; 549/75; 260/245.7; 549/77; 564/27; 260/330.3; 564/47; 564/56; 260/347.2; 564/82; 564/91; 260/347.3; 564/99; 564/104; 260/347.7; 564/108; 564/236; 260/326.25; 564/237; 564/238; 260/326.35; 564/340; 564/341; 260/326.36; 564/346; 564/347; 260/326.4; 260/326.55; 260/326.5 SF; 260/326.5 SM; 260/326.5 D; 260/326.5 L; 260/326.62; 260/326.82; 260/326.84; 260/326.85; 260/326.86; 424/267; 424/274; 424/275; 424/285; 424/304; 424/321; 424/322; 424/326; 424/330; 546/190
[58] Field of Search ............... 260/330.3, 347.2, 347.3, 260/347.7, 326.35, 326.36, 326.4, 326.5 SM, 239 B, 239 BF, 244.4, 245.7, 326.25, 326.55, 326.5 SF, 326.5 D, 326.5 L, 326.62, 326.82, 326.84, 326.85, 326.86; 424/267, 274, 275, 285, 244, 304, 321, 322, 326, 330; 546/214, 190, 191, 213, 230, 231; 549/65, 74, 75, 77; 564/27, 47, 56, 82, 91, 99, 104, 108, 236, 237, 238, 340, 341, 346, 347

[56] References Cited

U.S. PATENT DOCUMENTS 4,128,658 12/1978 Price et al. ......................... 424/285

Primary Examiner—Richard Raymond
Attorney, Agent, or Firm—Bacon & Thomas

[57] ABSTRACT

The invention provides compounds of general formula

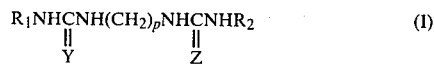

and physiologically acceptable salts, hydrates and bioprecursors thereof, in which Y and Z, which may be the same or different, each represent oxygen, sulphur, =CHNO₂ or =NR₃ where R₃ is hydrogen, nitro, cyano, lower alkyl, aryl, alkylsulphonyl or arylsulphonyl;

p has a value from 2 to 12;

R₁ represents

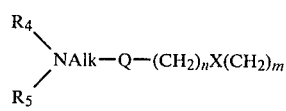

in which

R₄ and R₅ which may be the same or different, each represent hydrogen, lower alkyl, cycloalkyl, lower alkenyl, aralkyl or lower alkyl interrupted by an oxygen atom or a group >N-R₆ in which R₆ represents hydrogen or lower alkyl, or R₄ and R₅ together with the nitrogen atom to which they are attached form a 5 to 7-membered saturated heterocyclic ring which may contain an additional oxygen atom or the group >NR₆;

Q represents a furan or thiophen ring in which incorporation into the rest of the molecule is through bonds at the 2 and 5 positions, or a benzene ring in which incorporation into the rest of the molecule is through bonds at the 1 and 3 or 1 and 4 positions;

X represents —CH₂—, —O— or —S—;

n represents zero or 1;

m represents 2, 3 or 4 and Alk represents a straight chain alkylene group of 1 to 3 carbon atoms, and R₂ represents lower alkyl or the group

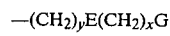

in which y represents 2, 3 or 4 or can additionally represent zero or 1 when E is a —CH₂— group, x represents zero, 1 or 2;

E represents —CH₂—, —O— or —S—; and

G represents a monocyclic 5 or 6 membered carbocyclic or heterocyclic aromatic ring, or G represents the group

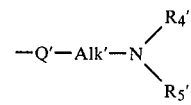

where Q' represents any of the rings defined for Q; Alk' represents any of the groups defined for Alk; and R₄' and R₅' which may be the same or different represent any of the groups defined for R₄ or R₅.

The compounds of formula (I) have pharmacological activity as selective histamine H₂-antagonists.

15 Claims, No Drawings

AMINE DERIVATIVES

This is a division of application Ser. No. 095,065, filed Nov. 16, 1979, now U.S. Pat. No. 4,264,614.

This invention relates to novel α,ω-disubstituted polymethylene compounds having action on histamine receptors, to processes for the preparation thereof, to pharmaceutical compositions containing them and to their use in therapeutics.

Certain novel α,ω-disubstituted polymethylene compounds have now been found which have potent activity as $H_2$-antagonists. These compounds, which are more particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in German Offenlegungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972, 236, 385. Furthermore the compounds antagonise the effect of histamine on the contraction frequency of isolated guinea pig right atrium but do not modify histamine induced contractions of isolated gastro-intestinal smooth muscle which are mediated via $H_1$-receptors.

Compounds with histamine $H_2$-blocking activity may be used in the treatment of conditions where there is a hypersecretion of gastric acid, particularly in gastric and peptic ulceration, as a prophylactic measure in surgical procedures, and in the treatment of allergic and inflammatory conditions where histamine is a known mediator. Thus they may be used for example, either alone, or in combination with other active ingredients in the treatment of allergic and inflammatory conditions of the skin.

The present invention provides compounds of general formula (I)

$$R_1NHCNH(CH_2)_pNHCNHR_2 \quad (I)$$
$$\underset{Y}{\|} \qquad \underset{Z}{\|}$$

and physiologically acceptable salts, hydrates and bioprecursors thereof, in which Y and Z, which may be the same or different, each represent oxygen, sulphur, =CHNO$_2$ or =NR$_3$ where R$_3$ is hydrogen, nitro, cyano, lower alkyl, aryl, alkylsulphonyl or arylsulphonyl;
p has a value from 2 to 12;
R$_1$ represents $$\underset{R_5}{\overset{R_4}{\diagdown}}NAlk-Q-(CH_2)_nX(CH_2)_m-$$

in which
R$_4$ and R$_5$ which may be the same or different, each represent hydrogen, lower alkyl, cycloalkyl, lower alkenyl, aralkyl or lower alkyl interrupted by an oxygen atom of a group >N-R$_6$ in which R$_6$ represents hydrogen or lower alkyl, or R$_4$ and R$_5$ together with the nitrogen atom to which they are attached form a 5 to 7-membered saturated heterocyclic ring which may contain an additional oxygen atom or the group >NR$_6$;
Q represents a furan or thiophen ring in which incorporation into the rest of the molecule is through bonds at the 2 and 5 positions, or a benzene ring in which incorporation into the rest of the molecule is through bonds at the 1 and 3 or 1 and 4 positions;
X represents —CH$_2$—, —O— or —S—;
n represents zero or 1;
m represents 2, 3 or 4 and Alk represents a straight chain alkylene group of 1 to 3 carbon atoms;
and R$_2$ represents lower alkyl or the group $$-(CH_2)_yE(CH_2)_xG$$

in which
y represents 2, 3, or 4 or can additionally represent zero or 1 when E is a —CH$_2$— group;
x represents zero, 1 or 2;
E represents —CH$_2$—, —O— or —S—; and
G represents a monocyclic or 5 or 6 membered carbocyclic or heterocyclic aromatic ring, or G represents the group $$-Q'-Alk'-N\underset{R_5'}{\overset{R_4'}{\diagup}}$$

where Q' represents any of the rings defined for Q;
Alk' represents any of the groups defined for Alk;
and R$_4'$ and R$_5'$ which may be the same or different represent any of the groups defined for R$_4$ and R$_5$.

Preferably when Q, Q' or G is a furan ring then x and n are not zero when X or E is oxygen.

The term 'lower' as applied to 'alkyl' means that the group has 1 to 6 carbon atoms, and in particular 1 to 4 carbon atoms, and when applied to 'alkenyl' that the group has 3 to 6 carbon atoms. The term 'aryl' as a group or part of a group preferably means phenyl or substituted phenyl, for example phenyl substituted with one or more alkyl, alkoxy or halogen groups. The monocyclic 5 or 6 membered carbocyclic or heterocyclic aromatic ring is preferably benzene, furan or thiophen.

According to one preferred aspect the invention provides compounds of formula (I) in which R$_1$ and R$_2$ may be the same or different and R$_1$ represents $$\underset{R_5}{\overset{R_4}{\diagdown}}NAlk-Q-(CH_2)_nX(CH_2)_m-$$

where R$_4$, R$_5$, Alk, Q, n, X and m are as defined in formula (I) and R$_2$ represents $$-(CH_2)_yE(CH_2)_x-Q'-Alk'N\underset{R_5'}{\overset{R_4'}{\diagup}}$$

where R$_4'$, R$_5'$, Alk', Q', X and E are as defined in formula (I) and y is 2, 3 or 4, with the proviso that n is not zero when X is oxygen and Q is a furan or thiophen ring system and x is not zero when E is oxygen and Q' is a furan or thiophen ring system.

Preferably R$_2$ represents

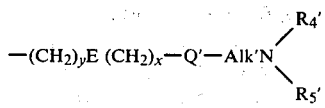

where R$_4'$, R$_5'$, Alk', Q', x and E are as defined in formula (I) and y is 2, 3 or 4 or R$_2$ represents an alkyl group, most preferably methyl. Preferably R$_4$, R$_5$, R$_4'$ and R$_5'$ are alkyl groups, most preferably methyl. Preferably Alk or Alk' is CH$_2$. Preferably m and y are 2 or 3. Preferably p is 3, 4 or 12. Preferably Y and Z are =CHNO$_2$ or =S and they are preferably the same. When Q or Q' is furan preferably n or X is 1, X or E is sulphur and m or y is 2. In this case preferably Y and Z are =CHNO$_2$ and p is 3 or 12. When Q or Q' is 1,3-benzene preferably n or x is zero, X or E is oxygen and m or y is 3. In this case preferably Y and Z are =CHNO$_2$ or =S and p is 3 or 4.

Particularly preferred compounds are N,N'-bis[1-[[2-[[5-[(dimethylamino)methyl]-2-furanyl-methyl]thio]ethyl]amino]-2-nitroethenyl]-1,3-propanediamine.

N,N'-bis[1-[[2-[[5-[(dimethylamino)methyl]-2-furanylmethyl]thio]ethyl]amino]-2-nitroethenyl]-1,12-dodecane diamine N,N'-bis[1-[[3-[3-[dimethylamino)methyl]phenoxy]-propyl]amino]-2-nitroethenyl]-1,4-butanediamine N-[2-[[5-[(dimethylamino)methyl]-2-furanylmethyl]-thio]ethyl]-N'-[12-[[1-(methylamino)-2-nitroethenyl-]amino]dodecyl]-2-nitro-1,1-ethene-diamine N,N''-1,3-propanediylbis-[N'-[3-[3-(dimethylamino)-methyl]phenoxy]propyl]thiourea].

The invention includes the compounds of formula (I) in the form of physiologically acceptable salts with inorganic and organic acids. Particularly useful salts include hydrochlorides, hydrobromides and sulphates; acetates, maleates, succinates, citrates and fumarates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers.

The compounds according to the invention, preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, e.g. H$_1$-antagonists.

Thus the compounds according to the invention may be formulated for oral, buccal, topical, parenteral or rectal administration. Parenteral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multidose containers, with an added preservative. The compositions may take such forms as suspensions solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays. Ointments and creams may for example, be formulated with an aqueous or oily base with the addition of suitable pharmaceutical excipients. Lotions may be formulated with an aqueous or oily base and will include the necessary adjustments to ensure pharmaceutically acceptable products. Spray compositions may, for example, be formulated as aerosols which may be pressurised by means of a suitable agent such as dichlorofluoromethane or trichlorofluoromethane or may be delivered by means of a hand-operated atomizer.

For internal administration a convenient daily dosage regime of the compounds according to the invention would be 2 to 4 doses to the total of some 200 mg to 2 g per day.

As will be appreciated by those skilled in the art, in the steps that follow it may be necessary to protect certain reactive substituents in the starting materials for a particular reaction and subsequently to remove the protecting group after completion of the reaction. Such protection and subsequent deprotection is especially pertinent when R$_4$ and/or R$_5$ or R$_4'$ and/or R$_5'$ are hydrogen in the grouping

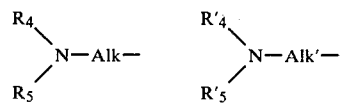

within the groups R$_1$ and/or R$_2$. Standard protection procedures may be employed e.g. formation of phthalimide (in the case of primary amines), N-benzyl, N-benzyloxycarbonyl, or N-trichloroethyloxycarbonyl derivatives. Subsequent cleavage of the protecting group is achieved by conventional procedures. Thus a phthalimide group may be cleaved by treatment with a hydrazine, e.g. hydrazine hydrate, or a primary amine, e.g. methylamine, N-benzyl or N-benzyloxycarbonyl derivatives may be cleaved by hydrogenolysis in the presence of a catalyst, e.g. palladium, and N-trichloroethyloxycarbonyl derivatives may be treated with zinc dust.

Compounds of formula (I) may be prepared by reacting an amine (II)

VNH$_2$      (II)

with a reagent (III)

WNAB      (III)

in which either
V represents the grouping

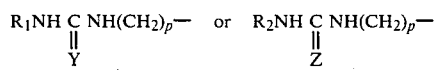

and
W represents $R_1$ or $R_2$ or
V represents $R_1$ or $R_2$ and
W represents the grouping

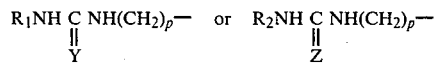

(in which $R_1$, $R_2$, Y, Z and p are as defined in formula (I). and A represents hydrogen and B represents

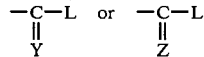

where L is a leaving group such as thiomethyl and Y and Z each represent $=CHNO_2$ or $=NR_3$ or A and B together represent $=C=Y$ or $=C=Z$ where Y and Z each represent $=O$ or $=S$, and $R_3$ is as defined in formula (I).

Embodiments of the above process are as follows:

Compounds of formula (I) in which $R_1$ is the same as $R_2$, Y is the same as Z and Y is $=NR_3$, or $=CHNO_2$ may be made by heating a diamine of formula (IV)

$$H_2N(CH_2)_pNH_2 \qquad (IV)$$

in which p is as defined above, with two molecular equivalents of a compound of formula (V)

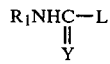

in which $R_1$ is as defined in formula (I), Y is $=CHNO_2$ or $=NR_3$ where $R_3$ is as defined in formula (I) and L is a leaving group such as thioalkyl, e.g. thiomethyl or alkoxy, e.g. ethoxy; preferably thiomethyl.

Compounds of formula (I) in which $R_1$ is the same as $R_2$, Y is the same as Z and Y is oxygen or sulphur may be made by reacting the diamine (IV) with two molecular equivalents of an isocyanate or isothiocyanate of formula (VI)

$$R_1N=C=Y \qquad (VI)$$

in which $R_1$ is as defined in formula (I) and Y is oxygen or sulphur, preferably in a solvent such as acetonitrile. An isocyanate of formula (VI) may be prepared by treating an amine of formula (VII)

$$R_1NH_2 \qquad (VII)$$

with phosgene and a base preferably triethylamine. An isothiocyanate of formula (VI) may be prepared by treating the amine (VII) as defined above with carbon disulphide followed by reaction with a chloroformate ester e.g. ethyl chloroformate or with decomposition of the intermediate formed with carbon disulphide using mercuric chloride and a base e.g. triethylamine.

Compounds of formula (I) in which $R_1$ differs from $R_2$ and/or Y differs from Z may be prepared by two-stage processes.

In order to prepare compounds of formula (I) in which $R_1$ is the same as $R_2$, Y differs from Z, and in which Y is $=CHNO_2$ or $=NR_3$ where $R_3$ is as defined in formula (I) a diamine of formula (IV) can be reacted with one molecular equivalent of a compound of formula (V) where $R_1$ and L are as defined and Y is $=CHNO_2$ or $=NR_3$ to produce an intermediate of formula (VIII)

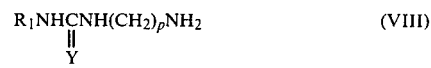

in which Y represents $=CHNO_2$ or $=NR_3$ which can then be reacted with one molecular equivalent of a compound of formula (IX)

in which L is a leaving group as defined above and Z differs from Y, the reaction being carried out in the absence or presence of a solvent e.g. water, dioxan, ethyl acetate or acetonitrile, at room temperature or above.

Alternatively, the intermediate of formula (VIII) could subsequently be reacted with a compound of formula (X)

$$R_1N=C=Z \qquad (X)$$

in which $R_1$ is as defined in formula (I) and Z is oxygen or sulphur, preferably in a solvent such as acetonitrile to give compounds of formula (I) in which $R_1$ is the same as $R_2$, Y differs from Z and Y is $=CHNO_2$ or $=NR_3$ and Z is O or S.

Similarly in order to prepare compounds of formula (I) in which $R_1$ differs from $R_2$, Y may or may not differ from Z and Y is $=CHNO_2$ or $=NR_3$ where $R_3$ is as defined in formula (I), an intermediate of formula (VIII) in which $R_1$ is as defined and Y is $=CHNO_2$ or $=NR_3$ may be reacted with one molecular equivalent of a compound of formula (XI) or (XII) respectively

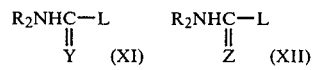

Alternatively the reaction may be carried out with compounds of formula (VIII), (XI) and (XII) in which $R_1$ is replaced by $R_2$ and $R_2$ is replaced by $R_1$.

Compounds of formulae (IX), (XI) and (XII) in which Y and Z are $=CHNO_2$ or $=NR_3$ may be prepared by reacting the appropriate amine of formula (VII) or (XIII)

$$R_2NH_2 \qquad (XIII)$$

with a compound of formula (XIV) or (XV)

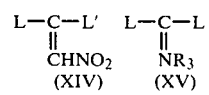

where $R_3$ and L are as defined in formula (III) and L' is as for L but may also be a group

where $R_6$ represents an alkyl group, the reaction being carried out in a solvent such as ether, acetonitrile, dioxan or ethyl acetate, at a temperature from ambient to reflux.

Compounds of formulae (IX), (XI) and (XII) in which Y and Z are oxygen or sulphur may be prepared from amines of formulae (VII) or (XIII) by conventional means, for example using phosgene or carbon disulphide followed by dimethylsulphate.

To prepare compounds of formula (I) in which $R_1$ is the same as $R_2$, Y is the same as Z and Y is sulphur, the amine of formula (IV) may be converted into a diisothiocyanate of formula (XVI)

where Y represents sulphur, by means described above for the preparation of isothiocyanates. The compound of formula (XVI) may then be reacted with two molecular equivalents of an amine of formula (VII) to give a compound of formula (I) in which Y is sulphur, $R_1$ is the same as $R_2$ and Y is the same as Z. Similarly, compounds of formula (I) in which Y is oxygen, $R_1$ is the same as $R_2$ and Y is the same as Z may be prepared from compounds of formula (IV) by reaction with phosgene and a base, for example triethylamine, to give an intermediate of formula (XVI) in which Y represents oxygen, followed by reaction with two molecular equivalents of the amine (VII).

Compounds of formula (I) in which $R_1$ differs from $R_2$ and/or Y differs from Z, and in which Y and Z are oxygen or sulphur may be prepared from an intermediate of formula (VIII) in which Y is oxygen or sulphur. This intermediate may be made by reacting an isocyanate or isothiocyanate of formula (VI) with excess of the diamine (IV). The compound of formula (VIII) in which Y is oxygen or sulphur is then reacted with the appropriate compound of formula (VI), i.e. $R_1N=C=Z$, $R_2N=C=Y$ or $R_2N=C=Z$.

In an alternative process to compounds of formula (I) in which $R_1$ is the same as $R_2$ an intermediate of formula (XVII)

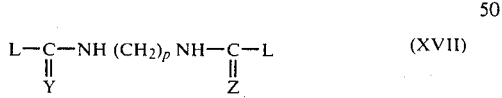

in which Y, Z, p and L are as defined in formulae (I) and (III), may be reacted with two molecular equivalents of an amine of formula (VII). The reaction may be carried out in a solvent, e.g. acetonitrile at elevated temperature, or, where Y and Z are $=CHNO_2$ in aqueous solution at room temperature.

The compounds of formula (XVII) in which p is preferably greater than 3, and Y and Z are the same and are $=CHNO_2$ or $=NR_3$ may be prepared by reacting an excess of a compound of formula (XIV) or (XV) with the diamine (IV). Compounds of formula (XVII) in which Y and Z are different and are $=CHNO_2$ or $=NR_2$ may be made by reacting an excess of the diamine (IV) with a compound of formula (XIV) with subsequent reaction of the intermediate so formed with a compound of formula (XV) or vice versa.

Compounds of formula (I) can also be prepared by reacting an amine of formula (VII) with a compound capable of converting the amino group into a group

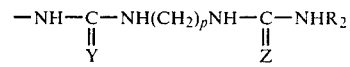

in which Y, Z, $R_2$ and p are as defined in formula (I). Compounds which are capable of this conversion are isocyanates, isothiocyanates or compounds of formula (XVIII)

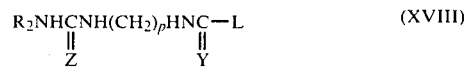

where Y represents $=NR_3$ or $=CHNO_2$ and L is a leaving group as defined above. The isocyanates and isothiocyanates will be of formula (XIX)

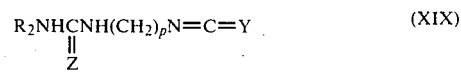

in which p is greater than 3, Y is oxygen or sulphur, and the reaction may be carried out by allowing the amine (VII) and isocyanate or isothiocyanate to react in a solvent such as acetonitrile. The reaction between the amine (VII) and a compound of formula (XVIII) where Y represents $=CHNO_2$ may be carried out by stirring the reactants in aqueous solution at room temperature. The reaction between the amine (VII) and a compound of formula (XVIII) may also be carried out by heating the reactants in the absence or presence of a solvent, e.g. acetonitrile, at a temperature of, for example 100° to 120° C.

Further processes for preparing the compounds of formula (I) are as follows:

Compounds of formula (I) in which, in $R_1$, n is 1, X is sulphur and other groups are as defined in formula (I) may be prepared from compounds of formulae (XX) or (XXI)

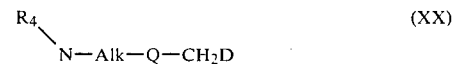

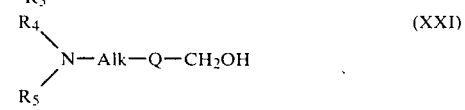

where $R_4$, $R_5$ and Q are as defined in formula (I) and D represents a leaving group such as halogen e.g. bromine or an acyloxy group e.g. acetoxy, using a thiol of formula (XXII)

The reaction between a thiol (XXII) and a compound of formula (XX) is preferably carried out in the presence of a strong base e.g. sodium hydride at room temperature in an organic solvent e.g. dimethylformamide.

The reaction between a thiol (XXII) and a compound of formula (XXI) is preferably carried out at 0° C. in a mineral acid e.g. concentrated hydrochloric acid. The starting materials of formula (XX) may be prepared from alcohols of formula (XXI) by conventional means.

Compounds of formula (I) in which, in at least one of $R_1$ and $R_2$, Q or Q' is a furan ring and Alk or Alk' is methylene and Y and Z are other than $=CHNO_2$ can be prepared from compounds of formula (XXIII)

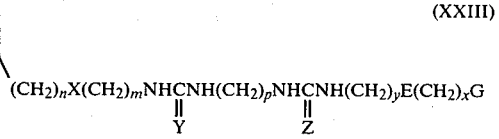
(XXIII)

by a Mannich reaction using formaldehyde and a secondary amine or a salt of a primary or secondary amine. The process may be carried out by reacting the amine salt with aqueous formaldehyde and the compound of formula (XXIII) or by refluxing the amine salt with paraformaldehyde in a suitable solvent, e.g. ethanol, with the compound of formula (XXIII). When G represents an unsubstituted furan ring the Mannich reaction can also take place at this ring.

Compounds of formula (I) in which, in at least one of $R_1$ and $R_2$, $R_4$ and $R_5$ or $R_4'$ and $R_5'$ are both methyl, Alk or Alk' is $CH_2$, and Q or Q' is furan or thiophen and Y and Z are other than $=CHNO_2$, can be prepared by treating a compound of formula (XXIV)

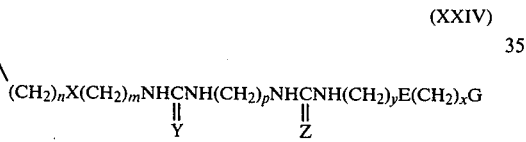
(XXIV)

where U represents oxygen or sulphur and Y and Z are other than $=CHNO_2$, with a reagent of formula (XXV)

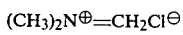 (XXV)

in a solvent e.g. acetonitrile at reflux temperature.

When G represents an unsubstituted thiophen or furan ring the group $(CH_3)_2NCH_2$ may also be added to this ring.

When the groups $R_4$ and $R_5$ or $R_4'$ and $R_5'$ in compounds of formula (I) are hydrogen they may be converted where appropriate into alkyl or aralkyl groups using, for example, an alkyl or aralkyl halide.

Amines of formulae (VII) and (XIII) may be prepared as described in German Offenlegungsschrift Nos. 2734070, 2821410 and 2821409 or by methods analogous to those described in these documents.

Where the product of any of the above processes is a free base and a salt is required, the salt may be formed in a conventional manner. Thus, for example, a generally convenient method of forming the salts is to mix appropriate quantities of the free base and the acid in an appropriate solvent(s), e.g. an alcohol such as ethanol or an ester such as ethyl acetate.

The invention is illustrated but not limited by the following Examples. In these examples the TLC data was obtained using silica plates "Polygram" SIL G/UV 254 0.25 mm thick.

EXAMPLE I (i) N,N'-Bis-[1-[[2-[[5-[(dimethylamino)methyl]-2-furanylmethyl]thio]ethyl]amino]-2-nitroethenyl]-1,12-dodecanediamine A mixture of N,N-dimethyl-5-[[[2-[(1-methylthio-2-nitroethenyl)amino]ethyl]thio]methyl]-2-furanmethanamine (2 g) and 1,12-diaminododecane (0.6 g) was heated at 100° for 3 hours. The oily residue was chromatographed (silica/methanol-0.88 ammonia, 79:1) to give an oil which solidified on trituration with ether giving the title compound (1.77 g) mp. 74°-76°.

Found: C,55.9; H,7.8; N,14.5; $C_{36}H_{62}N_8O_6S_2$ Requires: C,56.4; H,8.1; N,14.6%.

Similarly prepared were:

(ii) N,N'-Bis-[1-[[2-[[5-[(dimethylamino)methyl]-2-furanylmethyl]thio]ethyl]amino]-2-nitroethenyl]-1,10-decanediamine sulphate (0.68 g) as an oil from N,N-dimethyl-5-[[[2-[(1-methylthio-2-nitroethenyl)amino]ethyl]thio]methyl]-2-furanmethanamine oxalate (1.5 g) and 1,10-diaminodecane (0.25 g) in 8% aqueous bicarbonate (10 ml) at room temperature for 2 hours and 98°-100° for 4 hours followed by column chromatography (silica/methanol-0.88 ammonia, 79:1) and evaporation of eluates in the presence of ammonium sulphate.

TLC. (silica/methanol-0.88 ammonia, 79:1) Rf 0.37.

Found: C,51.6; H,7.8; N,13.9; $C_{34}H_{58}N_8O_6S_2 \cdot \frac{1}{2}H_2SO_4$ Requires: C,51.8; H,7.6; N,14.2%.

(iii) N,N'-Bis-[1-[[2-[[5-[(dimethylamino)methyl]-2-furanylmethyl]thio]ethyl]amino]-2-nitroethenyl]1,3-propanediamine (0.47 g), mp. 141°-145°, from N,N-dimethyl-5-[[[2-[(1-methylthio-2-nitroethenyl)amino]ethyl]thio]methyl]-2-furanmethanamine (1.5 g) and 1,3-diaminopropane (0.17 g) at 98°-100° for 2 hours followed by crystallisation from isopropanol.

Found: C,51.0; H,6.7; N,17.7; $C_{27}H_{44}N_8O_6S_2$ requires C,50.6; H,6.9; N,17.5%.

(iv) N,N'''-1,3-Propanediylbis-[N''-cyano-N'-[2-[[5-[(dimethylamino)methyl]-2-furanylmethyl]thio]ethyl]guanidine] (1 g) as a yellow oil from methyl N'-cyano-N-[2-[[5-[(dimethylamino)methyl]-2-furanylmethyl]thio]ethyl]carbaminidothioate (2 g) and 1,3-diaminopropane (0.24 g) at 98°-100° for 6 hours followed by column chromatography (silica/methanol).

TLC. (silica/methanol) Rf 0.19.

Found: C,52.9; H,7.2; N,22.5; $C_{27}H_{42}N_{10}O_2S_2 \cdot \frac{1}{2}H_2O$ requires: C,53.0; H,7.1; N,22.9%

(v) N,N'''-1,12-Dodecanediylbis-[N''-cyano-N'-[3-[3-[(dimethylamino)methyl]phenoxy]propyl]guanidine] (1.2 g) as yellow oil from methyl N'-cyano-N-[3-[3-[(dimethylamino)methyl]phenoxy]propyl]carbamimidothioate (2 g) and 1,12-diaminododecane (0.65 g) at 100° for 6 hours followed by column chromatography (silica/methanol)

TLC. (silica/methanol-0.88 ammonia, 79:1) Rf 0.5

Found: C,65.6; H,9.0; N,19.1; $C_{40}H_{64}N_{10}O_2 \cdot H_2O$ requires: C,65.4; H,9.1; N,19.1%

(vi) N,N-Bis[1-[[3-[3-[(dimethylamino)methyl]phenoxy]propyl]amino]-2-nitroethenyl]-1,4-butanediamine (1.05 g), mp. 146°-148° from N,N-dimethyl-3-[3-[[1-(methylthio)-2-nitroethenyl]amino]propoxy]benzenemethanamine (1.35 g) and 1,4-diaminobutane (0.183 g) in water (3 ml) and ethanol (3 ml) at room temperature for 4 days and crystallisation from ethanol.

Found: C,59.8; H,7.8; N,17.4; C₃₂H₅₀N₈O₆ requires: C,59.8; H,7.8; N,17.4%.

(vii) N,N'-Bis-[1-[[2-[[5-[(dimethylamino)methyl]-2-furanylmethyl]thio]ethyl]amino]-2-nitroethenyl]-1,6-hexanediamine (0.54 g) as an amber oil from N,N-dimethyl-5-[[[2-[(1-methylthio-2-nitroethenyl)amino]ethyl]thio]methyl]-2-furanmethanamine (1 g) and 1,6-hexanediamine in water (5 ml) at 98°–100° for 10 minutes followed by column chromatography (silica/methanol-0.88 ammonia, 79:1)

Found: C,50.2; H,7.3; N,15.2; C₃₀H₅₀N₈O₆S₂.2H₂O Requires: C,50.1; H,7.6; N,15.6%.

NMR. (CDCl₃) τ: 2.5–3.5 (2H,v.br.,2NH), 3.40(2H,s,2CH), 3.82(4H,s,4CH), 6.28(4H,s,2CH₂); 6.50(s,2CH₂), 6.20–7.50(br,6CH₂) (16H); 7.72(12H,s,4CH₃), 8.00–9.00 (8H,br,4CH₂).

(viii) N,N''''-1,12-Dodecanediylbis[N''-cyano-N'-[2-[[5-[(dimethylamino)methyl]-2-furanylmethyl]thio]ethyl]guanidine] (1.45 g) as an oil from methyl N'-cyano-N-[2-[[5-[(dimethylamino)methyl]-2-furanylmethyl]thio]ethyl]carbamimidothioate (2 g) and 1,12-diaminododecane (0.64 g) at 98°–100° for 3 hours followed by column chromatography (silica/methanol)

TLC. (silica/methanol-0.88 ammonia, 79:1) Rf 0.54.
NMR. (CDCl₃) γ: 3.90(4H,AB,4CH), 4.30(2H,t,2NH), 4.50(2H,t,2NH), 6.35(4H,s,2CH₂); 6.65(s,2CH₂), 6.73(q,2CH₂), 6.90(q,2CH₂)(12H); 7.37(4H,t,2CH₂). 7.80(12H,s,4CH₃), 8.8 region (20H,m,10CH₂).

EXAMPLE 2

(i) N,N''-1,3-Propanediylbis-[N'-[2-[[5-[(dimethylamino)methyl]-2-furanylmethyl]thio]ethyl]thiourea].

A mixture of 5-[[(2-isothiocyanatoethyl)thio]methyl]-N,N-dimethyl-2-furanmethanamine (2.56 g) and 1,3-diaminopropane (0.37 g) in acetonitrile (50 ml) was stirred at room temperature for 6 hours. The solvent was evaporated in vacuo and the residual oil chromatographed (silica/methanol) the appropriate eluate was evaporated in vacuo to give a yellow oil which on trituration with ether yielded the title compound (1.15 g) as a white powder.

TLC. (silica/methanol-0.88 ammonia, 79:1) Rf 0.54.
Found: C,51.0; H,7.2; N,14.1; C₂₅H₄₂N₆O₂S₄ requires: C,51.2; H,7.2; N,14.3%.

Similarly prepared was
(ii) N,N''-1,12-Dodecanediylbis-[N'-[2-[[5-[(dimethylamino)methyl]-2-furanylmethyl]thio]ethyl]thiourea] (3.0 g) as a white powder from 5-[[(2-isothiocyanatoethyl)thio]methyl]N,N-dimethyl-2-furanmethanamine (2.56 g) and 1,12-diaminododecane (1 g) in acetonitrile (50 ml).

TLC. (silica/methanol-ethyl acetate, 2:1) Rf 0.14.
Found: C,57.0; H,8.5; N,11.6; C₃₄H₆₀N₆O₂S₄ requires: C,57.3; H,8.5; N,11.8%.

EXAMPLE 3

N,N''-1,3-Propanediylbis-[N'-[3-[3-[(dimethylamino)methyl]phenoxy]propyl]thiourea]

A.
3-(3-Isothiocyanatopropoxy)-N,N-dimethylbenzenemethanamine

A solution of carbon disulphide (8.36 g) in acetone (16 ml) was added dropwise to a stirred solution of 3-(3-aminopropoxy)-N,N-dimethylbenzenemethanamine (20.8 g) in acetone (60 ml) at −10° to 0° during 15 minutes. A solution of mercuric chloride (27.2 g) in acetone (40 ml) was added slowly at −15° and after the addition the suspension was warmed to 0° and triethylamine (23 g) added dropwise. The suspension was refluxed for 45 minutes then filtered and evaporated to give an oil which was chromatographed (alumina, grade 3/ether). The appropriate eluate was evaporated to a yellow oil consisting of the title compound (8.7 g).

TLC. (alumina/ether) Rf 0.44.
NMR. (CDCl₃) τ: 2.77(1H,m,CH), 3.00–3.40(3H,m,3CH), 5.92(2H,t,CH₂), 6.26(2H,t,CH₂), 6.62(2H,s,CH₂); 7.77(s,2CH₃), 7.87(m,CH₂)(8H).

B.
N,N''-1,3-Propanediylbis-[N'-[3-[3-[(dimethylamino)methyl]phenoxy]propyl]thiourea]

A mixture of 3-(3-isothiocyanatopropoxy)-N,N-dimethylbenzenemethanamine (2.24 g) and 1,3-diaminopropane (0.42 g) in acetonitrile (50 ml) was stirred at room temperature for 24 hours. The solvent was evaporated in vacuo and the oily residue chromatographed (silica/methanol) to yield the title compound (0.46 g) as a gum.

TLC. (silica/methanol-0.88 ammonia, 79:1) Rf 0.58.
Found: C,60.6; H,8.3; N,14.5; C₂₉H₄₆N₆O₂S₂ requires: C,60.6; H,8.1; N,14.6%.

EXAMPLE 4

(i) N-[2-[[5-[(Dimethylamino)methyl]-2-furanylmethyl]thio]ethyl]-N'-[12-[[1-(methylamino)-2-nitroethenyl]amino]dodecyl]-2-nitro-1,1-ethenediamine.

A.(i)
N-[1-(Methylamino)-2-nitroethenyl]-1,12-dodecanediamine

A mixture of 1,12-diaminododecane (3 g) and N-methyl-1-(methylthio)-2-nitroethenamine (1.48 g) in water (50 ml) was stirred at room temperature for 20 hours. The solution was evaporated in vacuo and the residue chromatographed (silica/methanol). The appropriate eluate was evaporated to yield the title compound (1.8 g), mp. 123°–125°.

Found: C,60.2; H,10.9; N,18.4; C₁₅H₃₂N₄O₂ requires: C,60.0; H,10.7; N,18.6%.

Similarly prepared was:
(ii) N-[1-(Methylamino)-2-nitroethenyl]-1,6-hexanediamine (1 g), mp. 113°–115° from 1,6-diaminohexane (1.6 g) and N-methyl-1-(methylthio)-2-nitroethenamine (1.5 g) in water (50 ml) for 24 hours followed by column chromatography (silica/methanol).

TLC. (silica/methanol-0.88 ammonia, 79:1) Rf 0.1.

B.(i)
N-[2-[[5-[(Dimethylamino)methyl]-2-furanylmethyl]thio]ethyl]-N'-[12-[[1-(methylamino)-2-nitroethenyl]amino]dodecyl]-2-nitro-1,1-ethene diamine A mixture of N,N-dimethyl-5-[[[2-[(1-methylthio-2-nitroethenyl)amino]ethyl]thio]methyl]-2-furanmethanamine (0.8 g) and N-[1-(methylamino)-2-nitroethenyl]-1,12-dodecanediamine (0.8 g) was heated at 98°–100° for 4 hours. The oily residue was chromatographed (silica/methanol) and the appropriate eluate evaporated in vacuo to give a residue which was crystallised from methanol-ethyl acetate yielding the title compound (0.85 g), mp. 82°–85°.

Found: C,55.9; H,8.4; N,16.8; C₂₇H₄₉N₇O₅S requires: C,55.6; H,8.5; N,16.8%.

Similarly prepared was:

(ii) N-[2-[[5-(Dimethylaminomethyl)-2-furanylmethyl]thio]ethyl]-N'-[6-[[1-(methylamino)-2-nitroethenyl]amino]hexyl]-2-nitro-1,1-ethenediamine (1 g), m.p. 78°–80° from N,N-dimethyl-5-[[[2-[(1-methylthio-2-nitroethenyl)amino]ethyl]thio]methyl]-2-furanmethanamine (1.23 g) and N-[1-(methylamino)-2-nitroethenyl]-1,6-hexanediamine (0.8 g) in water (25 ml) for 24 hours followed by column chromatography (silica/methanol) and crystallisation from ethyl acetate-ethanol.

Found: C,50.1; H,7.8; N,19.4; $C_{21}H_{37}N_7O_5S$ requires: C,50.5; H,7.5; N,19.6%.

EXAMPLE 5

N-[1-[[2-[[5-[(Dimethylamino)methyl]-2-furanylmethyl]thio]ethyl]amino]-2-nitroethenyl]-N'-[[[3-[3-[(1-piperidinyl)methyl]phenoxy]propyl]amino]-2-nitroethenyl]-1,12-dodecanediamine

A.

N-[1-[[2-[[5-[(Dimethylamino)methyl]-2-furanylmethyl]thio]ethyl]amino]-2-nitroethenyl]-1,12-dodecanediamine A solution of N,N-dimethyl-[[[2-[(1-methylthio-2-nitroethenyl)amino]ethyl]thio]methyl]-2-furanmethanamine (1.99 g.) and 1,12-dodecyldiamine (4.8 g.) in ethanol (25 ml.) was stirred at room temperature for 7 days. The solution was evaporated in vacuo and the residue chromatographed (silica/methanol-0.880 ammonia, 19:1). The appropriate eluate was evaporated to give the title compound (2.2 g.) as a waxy semi-solid.

TLC (silica/methanol-0.880 ammonia, 19:1) $R_F$ 0.25.
Found: C,59.9; H,9.7; N,14.5; S,6.2; $C_{24}H_{45}N_5O_3S$ requires: C,59.6; H,9.4; N,4.15; S,6.6%.

B.

2-Nitro-N-[3-[3-(1-piperidinylmethyl)phenoxy]propyl]-1-(methylthio)etheneamine oxalate A mixture of 3-[3-[(1-piperidinyl)methyl]phenoxy]propanamine (4.97 g.) and 1,1-bis-(methylthio)-2-nitroethene (6.61 g.) in tetrahydrofuran (100 ml.) was heated under reflux for 19 hours. A solution of oxalic acid (6.25%) in tetrahydrofuran (4 ml.) was added, the suspension filtered and to the filtrate was added a solution of oxalic acid (6.25%) in tetrahydrofuran (36 ml.). The solid which separated on trituration was filtered, washed with tetrahydrofuran and dried to give the title compound (7.36 g.), m.p. 71°–75°.

TLC (silica/methanol-0.880 ammonia, 79:1) $R_F$ 0.65.
N.M.R. ($D_2O$): 2.50(1H,m,CH); 2.70–3.00(3H,m,3CH); 5.70(s,$CH_2$), 5.75(m,$CH_2$); 6.25(t,$CH_2$), 6.48(m,$CH_2$)(4H); 7.00(2H,m,$CH_2$), 7.45(3H,s,$CH_3$), 7.50–8.80(8H,m,4$CH_2$).

C.

2-Nitro-N-[3-[3-(1-piperidinylmethyl)phenoxy]propyl]-1-(methylthio)ethenamine

To a solution of 2-nitro-N-[3-[3-(1-piperidinylmethyl)phenoxy]propyl]-1-(methylthio)ethenamine oxalate (0.9 g.) in water (20 ml.) was added sodium bicabonate (3 g.). The suspension was extracted with ethyl acetate (2×20 ml.), the extracts dried ($Na_2CO_3$) and evaporated in vacuo to give the title compound (0.65 g.).

TLC (silica/methanol-0.880 ammonia, 79:1) $R_F$ 0.65.
N.M.R. ($CDCl_3$): 2.80(1H,m,CH), 3.00–3.30(3H,m,3CH), 3.40(1H,s,CH), 5.90(2H,t,$CH_2$), 6.40(21 H,q,$CH_2$), 6.50(2H,s,$CH_2$); 7.55(s,$CH_3$), 7.60(m,2$CH_2$), 7.80(m,$CH_2$) (9H); 8.30–8.70(6H,m,3$CH_2$).

D.

N-[1-[[2-[[5-[(Dimethylamino)methyl]-2-furanylmethyl]thio]ethyl]amino]-2-nitroethenyl]-N'-[[[3-[3-[(1-piperidinyl)methyl]phenoxy]propyl]amino]-2-nitroethenyl]-1,12-dodecanediamine A mixture of 2-nitro-N-[3-[3-(1-piperidinylmethyl)phenoxy]propyl]-1-(methylthio)ethenamine (0.58 g.) and N-[1-[[2-[[5-[(dimethylamino)methyl]-2-furanylmethyl]thio]ethyl]amino]-2-nitroethenyl]-1,12-dodecanediamine (0.77 g.) in methanol (3 ml.) was evaporated and the residue heated at 98°–100° for 6 hours. The oily residue was chromatographed (silica/methanol-0.880 ammonia, 79:1) and the appropriate eluate evaporated in vacuo to give the title compound (0.8 g.) as an oil.

TLC (silica/methanol-0.880 ammonia, 79:1) $R_F$ 0.5.
Found: C, 60.4; H, 8.9; N, 13.5 $C_{41}H_{68}N_8O_6S.H_2O$ requires: C, 60.1; H, 8.6; N, 13.7%.

NMR ($CDCl_3$)τ: −0.32 (2H, m, 2NH), 2.80 (1H, m, CH), 2.80–3.50 (7H, m, 2NH and 5 CH), 3.90 (2H, m, 2CH), 5.96 (2H, t, $CH_2$); 6.31 (s, $CH_2$), 6.40–6.71 (m, 4$CH_2$), 6.60 (s, 2$CH_2$) (14H); 7.29 (2H, m, $CH_2$); 7.40–8.10 (m, 3$CH_2$), 7.78 (s, 2$CH_3$) (12H); 8.10–9.00 (26H, m, 13$CH_2$).

EXAMPLE 6

N-[1-[[2-[[[5-[(Dimethylamino)methyl]-2-furanyl]methyl]thio]ethyl]amino]-2-nitroethenyl]-N'-[1-[[2-[(2-furanylmethyl)thio]ethyl]amino]-2-nitroethenyl]-1,12-dodecanediamine

A.

N-2-[[(2-Furanyl)methyl]thio]ethyl-1-(methylthio)-2-nitroethenamine

A solution of 2-[(2-furanylmethyl)thio]-2-nitroethenamine (3.14 g.) and 1,1-bis-(methylthio)-2-nitroethane (13.2 g.) in dioxan (100 ml.) was heated at 100° for 1½ hours. The solution was evaporated in vacuo and the residue suspended in warm ethyl acetate (70 ml.). The cooled suspension was filtered and the filtrate evaporated in vacuo. The oily residue was suspended in ether and the solid which separated was filtered and crystallised from ethanol to give the title compound (2.17 g.), m.p. 68°–70°.

TLC (silica/ether-cyclohexane, 4:1) $R_F$ 0.3.
Found: C, 43.5; H, 5.2; N, 10.1; $C_{10}H_{14}N_2O_3S_2$ requires: C, 43.8; H, 5.1; N, 10.2%.

B.

N-[1-[[2-[[[5-[(Dimethylamino)methyl]-2-furanyl]methyl]thio]ethyl]amino]-2-nitroethenyl]-N'-[1-[[2-[(2-furanylmethyl)thio]ethyl]amino]-2-nitroethenyl]-1,12-dodecanediamine A mixture of N-[1-[[2-[[5-[(dimethylamino)methyl]-2-furanylmethyl]thio]ethyl]amino]-2-nitroethenyl]-1,12-dodecanediamine (0.8 g.) and N-2-[[(2-furanyl)methyl]thio]ethyl-1-(methylthio)-2-nitroethenamine (0.57 g.) in ethyl acetate (8 ml.) was evaporated and the residue heated at 98°–100° for 2 hours. The oily residue was dissolved in methanol (10 ml.) and evaporated to dryness (×2). The oily residue was triturated with ethyl acetate (30 ml.), the solid which separated was washed with ethyl acetate and dried to give the title compound (0.82 g.), m.p. 69°–72°.

TLC (silica/methanol) $R_f$ 0.35.

NMR(CDCl$_3$)τ: −0.70−0.00 (2H, m, 2NH), 2.70−3.20(2H, m, 2NH), 2.60(1H, brs, CH), 3.40(2H, brs, 2CH), 3.60−3.90(4H, m, 4CH), 6.28(4H, brs, 2CH$_2$); 6.30−7.00(m, 4CH$_2$), 6.60(s, CH$_2$) (10H); 7.27(4H, t, 2CH$_2$), 7.75(6H, s, 2CH$_2$), 8.10−9.00(20H, m, 10CH$_2$).

Pharmaceutical Compositions

1. Tablets

| a. | Direct Compression | mg/tablet |
|---|---|---|
| | Active ingredient | 200.00 |
| | Microcrystalline cellulose BPC | 198.00 |
| | Magnesium stearate | 2.00 |
| | Compression weight | 400.00 |

The active ingredient is sieved through a 250 μm sieve, blended with the excipients and compressed using 10.0 mm punches. Tablets of other strengths may be prepared by altering the compression weight and using punches to suit.

| b. | Wet Granulation | mg/tablet |
|---|---|---|
| | Active ingredient | 200.00 |
| | Lactose B.P. | 138.00 |
| | Starch B.P. | 40.00 |
| | Pregelatinized Maize starch B.P. | 20.00 |
| | Magnesium Stearate B.P. | 2.00 |
| | Compression weight | 400.00 |

The active ingredient is sieved through a 250 μm sieve and blended with the lactose, starch and pregelatinised starch. The mixed powders are moistened with purified water, granules are made, dried, screened and blended with the magnesium stearate. The lubricated granules are compressed into tablets as described for the direct compression formulae.

The tablets may be film coated with suitable film forming materials, e.g. methyl cellulose or hydroxypropyl methyl cellulose using standard techniques. Alternatively the tablets may be sugar coated.

| 2. | Capsules | mg/capsule |
|---|---|---|
| | Active ingredient | 200.00 |
| | *STA-RX 1500 | 100.00 |
| | Magnesium Stearate B.P. | 1.50 |
| | Fill Weight | 300.00 mg. |

*A form of directly compressible starch supplied by Colorcon Ltd., Orpington, Kent.

The active ingredient is sieved through a 250 μm sieve and blended with the other materials. The mix is filled into No. 2 hard gelatin capsules using a suitable filling machine. Other doses may be prepared by altering the fill weight and if necessary changing the capsule size to suit.

| 3. Syrup | | mg/5ml dose |
|---|---|---|
| Active ingredient | | 200.00 |
| Sucrose B.P. | | 2750.00 |
| Glycerine B.P. | | 500.00 |
| Buffer | | |
| Flavour | | |
| Colour | as required | |
| Preservative | | |
| Distilled Water | | 5.00ml |

The active ingredient, buffer, flavour, colour and preservative are dissolved in some of the water, and the glycerine is added. The remainder of the water is heated to 80° C. and the sucrose is dissolved in this and cooled. The two solutions are combined, adjusted to volume and mixed. The syrup produced is clarified by filtration.

| 4. Injection for Intravenous Administration | % w/v |
|---|---|
| Active ingredient | 1.00 |
| Water for injection B.P. to | 100.00 |

Sodium chloride may be added to adjust the tonicity of the solution and the pH may be adjusted to that of maximum stability and/or to facilitate solution of the active ingredient using either dilute acid or alkali.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

We claim:

1. Compounds of the general formula (I)

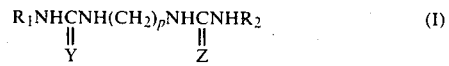

or a physiologically acceptable salt or hydrate thereof, in which

Y and Z, which may be the same or different, each represent oxygen, sulphur, =CHNO$_2$ or =NR$_3$ where R$_3$ is hydrogen, nitro, cyano, lower alkyl, aryl, alkylsulphonyl or arylsulphonyl; p has a value from 2 to 12; R$_1$ represents

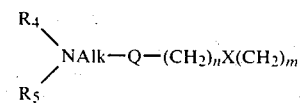

in which

R$_4$ and R$_5$, which may be the same or different each represent hydrogen, lower alkyl, cycloalkyl, lower alkenyl, aralkyl or lower alkyl interrupted by an oxygen atom or a group >N-R$_6$ in which R$_6$ represents hydrogen or lower alkyl, or R$_4$ and R$_5$ together with the nitrogen atom to which they are attached form a 5 to 7-membered saturated alkyleneimine ring; Q represents a benzene ring in which incorporation into the rest of the molecule is through bonds at the 1 and 3 or 1 and 4 positions;

X represents —CH$_2$—, —O— or —S—;

n represents zero or 1;

m represents 2, 3 or 4; and

Alk represents a straight chain alkylene group of 1 to 3 carbon atoms;

and R$_2$ represents lower alkyl or the group

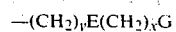

in which y represents 2, 3 or 4, or can additionally represent zero or 1 when E is a —CH$_2$— group;

x represents zero, 1 or 2;

E represents —CH$_2$—, —O— or —S—; and

G represents a monocyclic 5 or 6 membered carbocyclic aromatic ring, or a thiophen or furan ring, or G represents the group

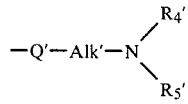

where Q' represents a thiophen ring in which incorporation into the rest of the molecule is through bonds at the 2- and 5-positions, or a benzene ring in which incorporation into the rest of the molecule is through bonds at the 1 and 3 or 1 and 4 positions; Alk' represents any of the groups defined for Alk; and R$_4$' and R$_5$', which may be the same or different, represent any of the groups defined for R$_4$ or R$_5$.

2. Compounds according to claim 1 in which in the substituent R$_2$ when G is a furan ring, when x is not zero when E is oxygen.

3. Compounds according to claim 1 in which R$_2$ represents

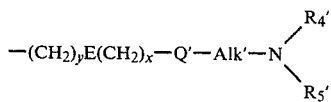

where R$_4$', R$_5$', Alk', Q', x and E are as defined in claim 1 and y is 2, 3 or 4.

4. Compounds according to claim 1 in which R$_2$ represents an alkyl group.

5. Compounds according to claim 1 in which R$_4$, R$_5$, R$_4$', and R$_5$' are alkyl groups.

6. Compounds according to claim 1 in which Alk and/or Alk' is CH$_2$.

7. Compounds according to claim 1 in which m and y are 2 or 3.

8. Compounds according to claim 1 in which p is 3, 4 or 12.

9. Compounds according to claim 1 in which in the substituent R$_1$, n is zero, X is oxygen and m is 3, and in the substituent R$_2$, Q' is 1,3-benzene, x is zero, E is oxygen and y is 3.

10. Compounds according to claim 9 in which Y and/or Z is =CHNO$_2$ or =S and p is 3 or 4.

11. Compounds according to claim 1 which are: N,N'-bis[1-[[3-[3-[(dimethylamino)methyl]phenoxy]propyl]amino]-2-nitroethenyl]-1,4-butanediamine or N,N''-1,3-propanediylbis-[N'-[3-[3-[(dimethylamino)methyl]phenoxy]propyl]thiourea].

12. Compounds according to claim 1 in which R$_1$ and R$_2$ may be the same or different and R$_1$ represents

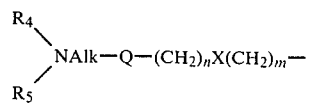

where R$_4$, R$_5$, Alk, Q, n, X and m are as defined in formula (I) and R$_2$ represents

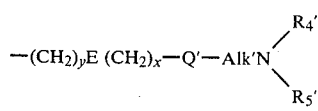

where R$_4$', R$_5$', Alk', Q', x and E are as defined in claim 1 and y is 2, 3 or 4 with the proviso that x is not zero when E is oxygen and Q' is a thiophen ring system.

13. A pharmaceutical composition comprising an effective amount of a compound according to claim 1 together with at least one pharmaceutically acceptable carrier or diluent, and optionally an effective amount of at least one other active ingredient.

14. A pharmaceutical composition as claimed in claim 13 in which the compound as claimed in claim 1 is in the form of a physiologically acceptable salt.

15. A method of treating a condition mediated through histamine H$_2$-receptors which comprises administering to a patient an effective amount of a compound as defined in claim 1 to relieve said condition.

* * * * *